United States Patent [19]

Frater

[11] Patent Number: 5,415,667
[45] Date of Patent: May 16, 1995

[54] MITRAL HEART VALVE REPLACEMENTS

[76] Inventor: Robert W. M. Frater, 17 Gladwin Pl., Bronxville, N.Y. 10708

[21] Appl. No.: 965,419
[22] PCT Filed: Jun. 4, 1991
[86] PCT No.: PCT/US91/03834
§ 371 Date: Dec. 29, 1992
§ 102(e) Date: Dec. 29, 1992
[87] PCT Pub. No.: WO91/19465
PCT Pub. Date: Dec. 26, 1991

[30] Foreign Application Priority Data

Jun. 7, 1990 [GB] United Kingdom ............... 9012716

[51] Int. Cl.6 ........................................ A61F 2/24
[52] U.S. Cl. ............................................. 623/2
[58] Field of Search ................................. 623/1-3, 623/900, 2

[56] References Cited

U.S. PATENT DOCUMENTS 3,656,185  4/1972  Carpentier ............... 623/2
3,898,701  8/1975  La Russa ................. 623/2
4,790,844 12/1988  Ovil ........................ 623/2
4,960,424 10/1990  Grooters ................. 623/2

Primary Examiner—David Isabella
Assistant Examiner—Elizabeth M. Burke
Attorney, Agent, or Firm—Trexler, Bushnell, Giangiorgi & Blackstone, Ltd.

[57] ABSTRACT

A mitral heart valve replacement of essentially flexible bioincorporable material comprising a generally D-shaped (30) sewing ring having an opening (31) with at least one long straight side portion (32), an anterior cusp (33) hinged contiguously from that straight side portion (32) a posterior cusp (34) hinged contiguously from a shorter side portion (35) of the opening (31) opposite the anterior cusp (33), and two lateral cusps (36A & 36B) hinged contiguously one from each of the remaining side portions of the opening (31) extending between adjacent ends of the side portions (35) from which the anterior (33) and posterior cusps (34) are hinged, together with chordae of bioincorporable material extending from edge portions of the cusps for connection to the papillary muscles in the cavity of the ventricle when the sewing ring is sutured to the atrio-ventricular junction of the host or patient heart.

22 Claims, 5 Drawing Sheets

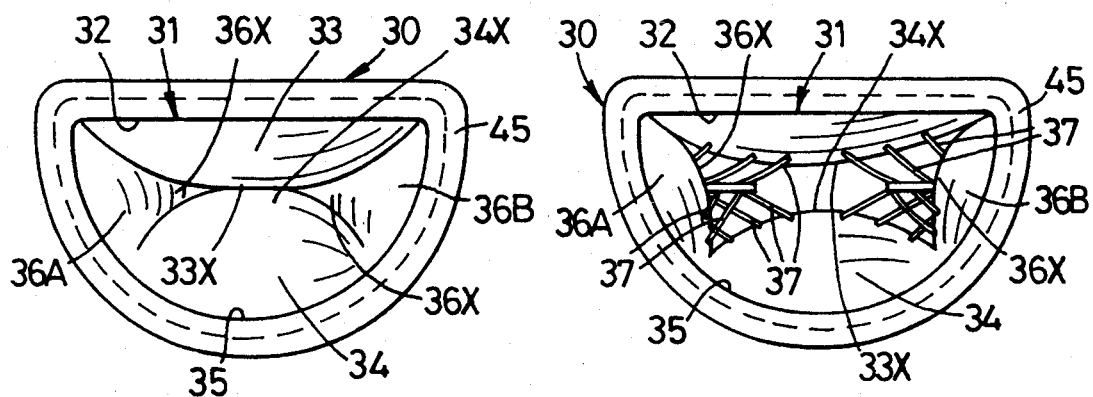
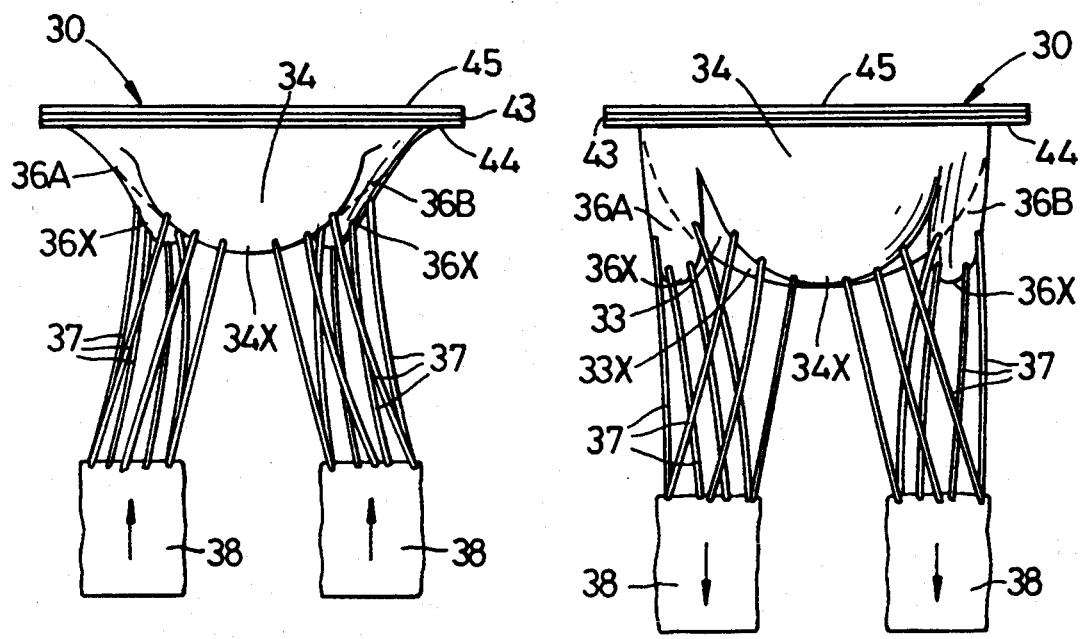

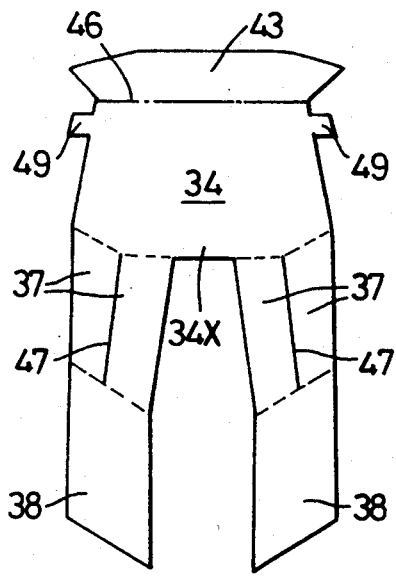
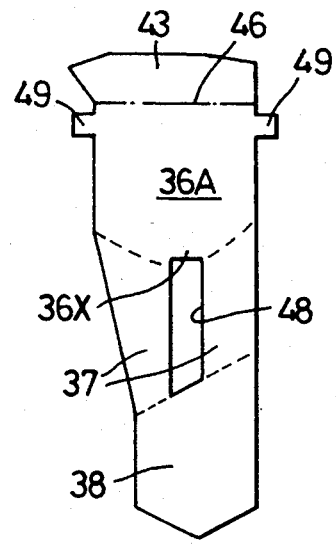
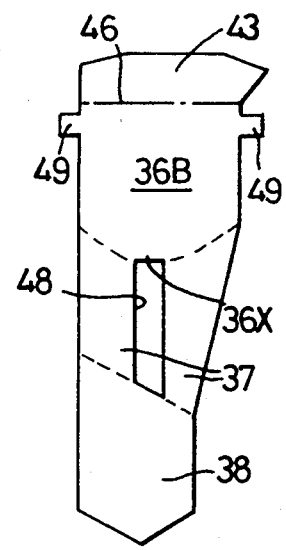
Fig. 9　　　　　Fig. 10　　　Fig. 11
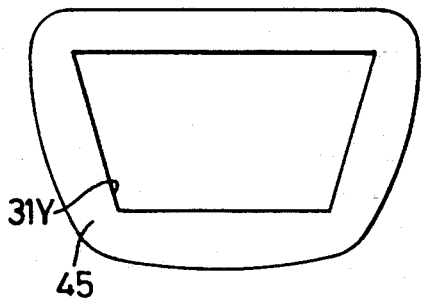
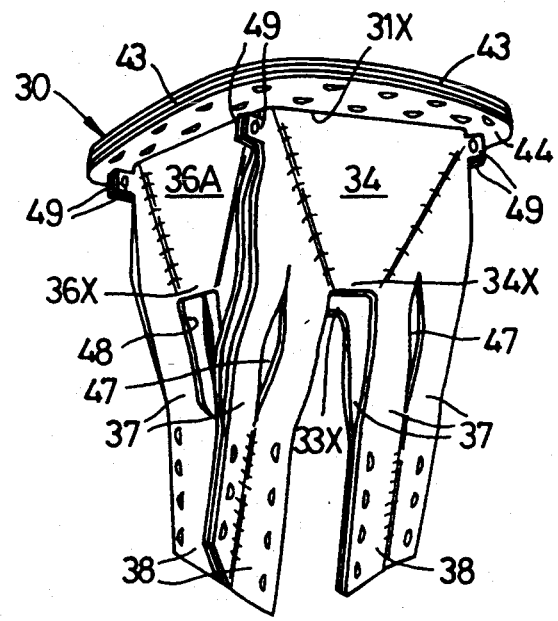
Fig. 12　　　　　Fig. 13

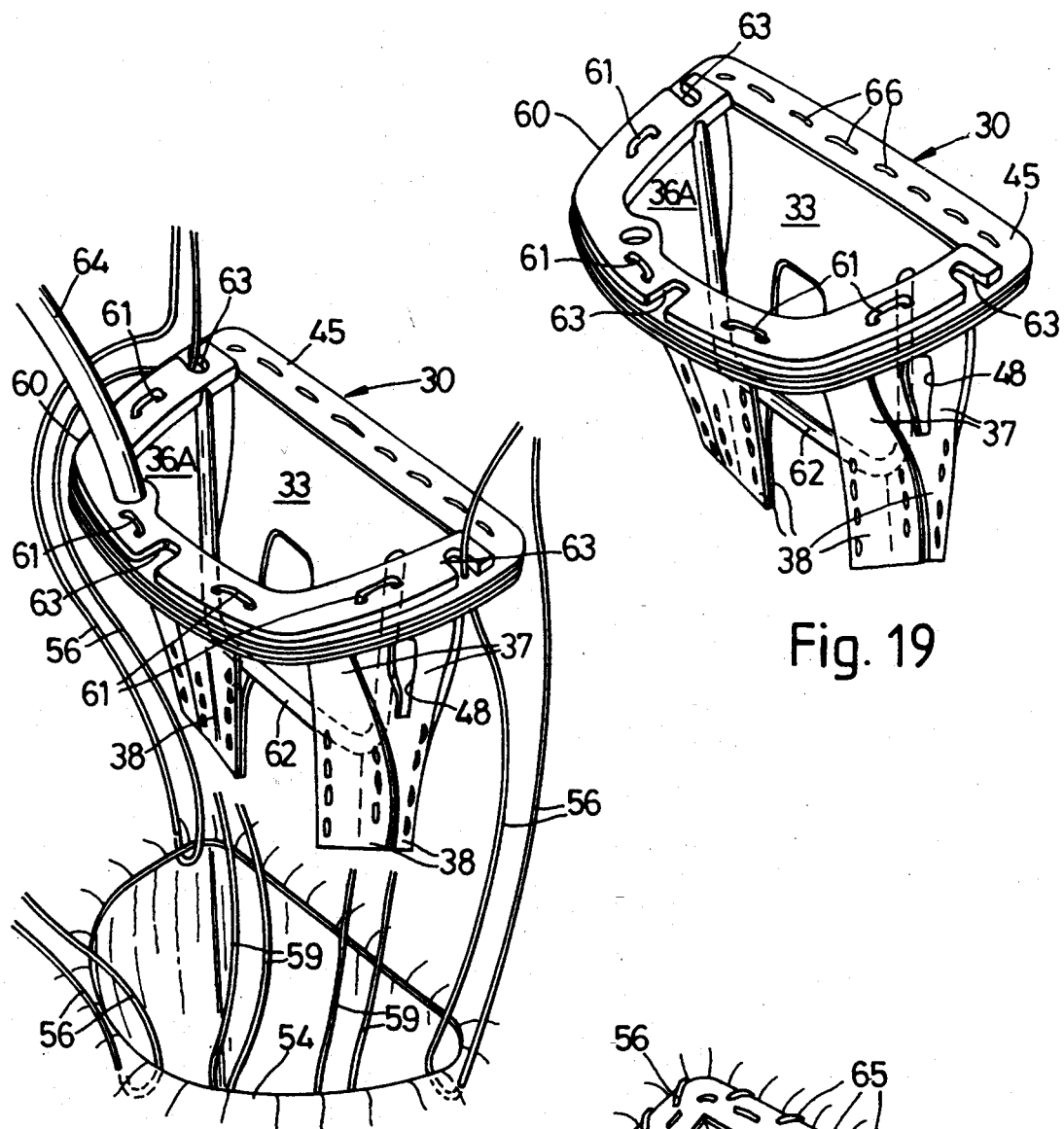
Fig. 19
Fig. 20
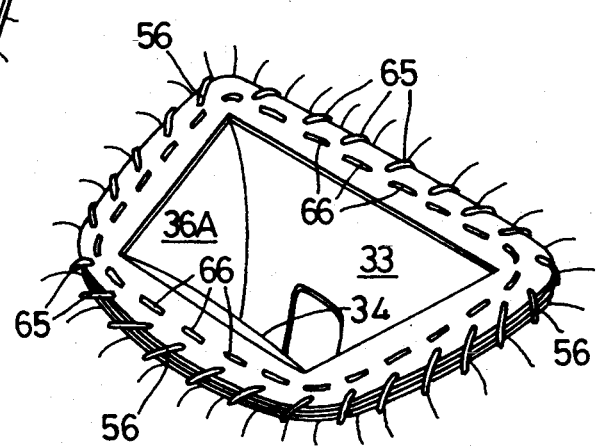
Fig. 21

MITRAL HEART VALVE REPLACEMENTS

This invention relates to mitral heart valve replacements.

Heart valve replacement and in particular mitral valve replacement devices fall into two broad categories, mechanical and bioprosthetic. Both kinds of device are obstructive to flow compared with the normal natural valve.

Mechanical valves of all kinds must be used with coumadin type anticoagulants: without this treatment there is a prohibitive risk of the formation of clots which will either obstruct the valve or break away to block vital arteries (e.g., arteries in the brain, leading to a stroke). Even with anticoagulants the risk of clotting and its complications remains. The durability of most mechanical valves is excellent.

Bioprosthetic valves (of treated biological tissue supported by a frame or stent) are less likely to be affected by clot formation but have less durability, inevitably developing calcification and/or tears with time, with this process being prohibitively accelerated in children.

The haemodynamics of the natural mitral valve are dependent on the absence of a stent, the absence of a rigid ring, the relatively unrestrained opening of the flaps and the flexibility of the tissues. The durability is dependent on the fact that it is living tissue capable of self regeneration. The absence of clotting problems is related to the living endothelium which is composed of special cells with properties that prevent local clot formation.

One object of the present invention is to provide an entirely flexible non-elastic bioincorporable unstented replacement mitral valve that has no rigid parts to project into the inner cavity of the ventricle.

Another object is to avoid the use of any metal or plastics stiffener in the circumferential part of the replacement valve that is to be sewn to the orifice of the ventricle.

A further object is to provide a replacement mitral heart valve in which the part to be fixed to the inlet orifice of the ventricle is an integral part of and is in continutity with the valve mechanism proper, and therefore:

a) has no bulk to detract from the effective orifice area of the valve;

b) has a smooth inflow into the orifice without any potential nooks and crannies or excrescence that can produce local stasis that leads to thrombus formation;

c) has no interface between bioincorporable and non-bioincorporable material that when it exists is always accompanied by clot formation;

d) allows healing to take place directly between the bioincorporable implant and the native tissue, thereby, ensuring a permanent secure bond between body and implanted valve that is not dependent on the continued integrity of the sutures used for insertion.

Yet another object of the invention is to provide a form of valve whereby one size fits more than one size of patient heart, and which has the parts to be stitched to the heart marked to indicate the correct placement of sutures for a particular heart size.

A still further object is to provide a combined sizing and suture placement guiding device which indicates the correct placement of sutures to ensure optimal opening and closing of the respective valve.

According to the principal aspect of the present invention, a mitral heart valve replacement of essentially flexible bioincorporable material comprises a generally D-shaped sewing ring having an opening with at least one long straight side portion, an anterior cusp hinged contiguously from that straight side portion, a posterior cusp hinged contiguously from a shorter side portion of the opening opposite the anterior cusp, and two lateral cusps hinged contiguously one from each of the remaining side portions of the opening extending between adjacent ends of the side portions from which the anterior and posterior cusps are hinged, together with chordae of bioincorporable material extending from edge portions of the cusps for connection to the papillary muscles in the cavity of the ventricle when the sewing ring is sutured to the atrio-ventricular junction of the host or patient heart, the aggregate area of the cusps exceeding the area bounded by the sewing ring so that when the valve is caused to open, by the papillary muscles pulling the chordae, the cusps simply deflect away from each other, and when the papillary muscles allow the valve to close, the edge portions of the cusps meet out of the plane of the sewing ring so as to be capable of meeting in the cavity of the ventricle of the patient heart.

The anterior cusp is preferably contiguous with one-third of the perimeter of the sewing ring opening and preferably has a generally semicircular edge portion to enable it to project deeply into the cavity of the ventricle; and the posterior and lateral cusps—which are, therefore, together contiguous with two-thirds of the perimeter of the sewing ring opening—preferably also have generally semicircular edges portions.

The sewing ring opening may be truly D-shaped, and may be matched by a correspondingly larger D-shaped external profile to suit the atrio-ventricular junction in a patient heart. Preferably, however, the opening is trapezium-shaped, to provide longer and shorter parallel straight side portions from which are hinged the anterior and posterior cusps respectively, and two even shorter non-parallel side portions from which are hinged the anterior and posterior cusps respectively, and two even shorter non-parallel side portions from which are hinged the lateral cusps, while the sewing ring has a more truly D-shaped external profile to suit the atrio-ventricular junction in a patient heart. Making the sides of the sewing ring opening straight ensures minimal bending of the cusps and an absence of undesirable folds or creases during movement back and forth between open and closed positions.

The sewing ring may be formed by a combination of integral flange portions of the anterior, posterior and lateral cusps stitched to a flat basic ring element cut from the bioincorporable material, preferably with a similar flat reinforcing or stiffening element of biocompatible material between which and the basic ring element the flange portions of the cusps are interposed. The posterior cusp and the lateral cusps and their flange portions may be formed from a flat strip of the bioincorporable material, with spacer portions between adjacent cusp portions, which spacer portions are partially cut through and/or pleated and stitched so that the integral flange portion can conform to the arcuate portion of a D-shaped opening, and to bring the adjacent cusp portions into contiguous disposition with each other.

The chordae may be separate chords attached by sewing to the edge portions of the cusps and to attachment portions adapted to be eventually sewn to the papillary muscles, but are preferably formed integral with the cusps and are provided with integral attachment portions at the ends remote from the cusps for suturing to the papillary muscles. The cusps, chordae and attachment portions may be provided with non-elastic reinforcing strands running from the cusps to the attachment portions. Similar strands may also run from side to side of the cusps adjacent their free edges or across the middle. The attachment portions may be attached to the papillary muscles with their adjacent edges together or apart, depending on the shape and form of the papillary muscles. When the host anatomy allows the adjacent edges to be spaced apart, this arrangement allows for the largest possible area for flow of blood.

The bioincorporable material may be biological material, such as auto, homo or zenograft pericardial tissue treated with glycerol (possibly reinforced by bio-incorporable non-elastic sutures, such as extruded polytetrafluoroethylene sutures to guard against stretching), so as to allow the host to cover the valve with living self-repairing fibrous tissue and on this a growth of new endothelium presenting a surface to the blood that does not clot. Alternatively, the valve may be made of a non-biological material that allows the host to provide a cover of fibrous tissue and endothelium leaving the implanted material completely covered by natural host tissue.

Because of the great flexibility of the valve in accordance with the invention one size may be used for several sizes of patient heart; thus the sewing ring may be provided with a central marker line (e.g., a broken line, formed by an interwoven suture) to indicate inner and outer stitching zones for different ranges of heart size. Two sizes of valve in accordance with the invention may thus suffice for the full range of patient heart sizes.

A rigid holder is preferably temporarily secured to the sewing ring and has a generally U-shaped bar extending between the chordae of the anterior and posterior cusps as far as the attachment portions, so as to prevent collapsing of the valve, particularly during placement in the patient heart. The temporary securing of the holder to the sewing ring may be effected by tacking stitches which are cut and removed when the valve has been secured in place. The holder is preferably provided with notches or slots for location of sutures through the sewing ring and the holder preferably has a detachable handle used during placement of the valve in the patient heart.

According to another aspect of the present invention there is provided a combined sizing and suture placement guiding device comprising an elongate handle carrying an arcuate sizing member having a circumferential shallow groove for fitting within the corresponding part of the remnant of the excised natural valve of the patient heart at the atrio-ventricular junction, with notches or slots, one adjacent each end of the sizing member and one intermediate thereof, for indicating the positions for placement sutures to be passed also through corresponding positions on the sewing ring of a replacement valve in accordance with the first aspect of the invention, and with a depth guage depending from the sizing member for contact with the papillary muscles to indicate the positions of placement sutures in the papillary muscles for securing the attachment portions of the chordae.

A number of embodiments of the invention and their manner of use will not be described, by way of example only, with reference to the accompanying drawings, in which:

FIGS. 1 and 2 are diagrammatic plan and posterior views respectively of an embodiment of the invention, the valve being shown closed;

FIGS. 3 and 4 correspond to FIGS. 1 and 2 respectively but with the valve shown open;

FIGS. 5 and 6 correspond to FIGS. 2 and 4 respectively but show another embodiment of the invention;

FIGS. 7 to 12 are templates of the component parts of a preferred embodiment of the invention, a perspective view of which from below forms FIG. 13;

FIG. 19 is a perspective view from above of the preferred embodiment of valve temporarily fitted with a holder;

FIG. 20 corresponds to FIG. 19 but shows the holder being used to position sutures through the sewing ring of the valve, and with other sutures through the remnant of the excised natural valve; and FIG. 21 is a fragmentary perspective view showing the valve secured in position after detaching the temporary holder.

Figure 14:
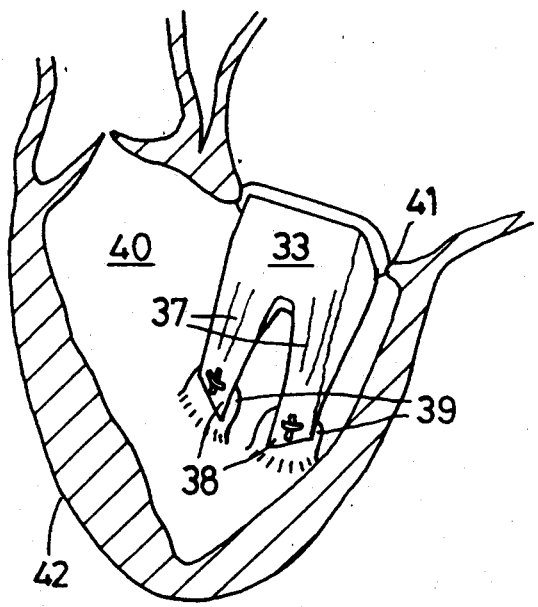
FIG. 14 is a fragmentary diagrammatic section through a patient heart showing the preferred embodiment of valve in position at the atrio-ventricular junction.
Figure 15:
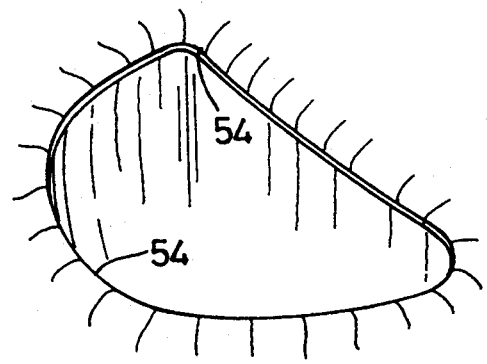
FIG. 15 is a fragmentary perspective view showing the remnant of the excised natural valve of the patient heart at the atrio-ventricular awaiting fitting of a valve in accordance with the invention.

In FIGS. 1 to 4, a mitral heart valve replacement is formed of essentially flexible bioincorporable material and comprises a generally D-shaped sewing ring 30 having an opening 31 with one straight side portion 32, an anterior cusp 33 hinged contiguously from that straight side portion, a posterior cusp 34 hinged contiguously from a shorter portion of the arcuate side 35 of the opening opposite the anterior cusp, and two lateral cusps 36A and 36B hinged contiguously one from each of the remaining portions of the arcuate side 35 of the opening extending between adjacent ends of the side portions from which the anterior and posterior cusps are hinged, together with chordae 37 of bioincorporable material extending from edge portions 33X, 34X and 36X of the cusps 33, 34, 36A and 36B for connection through attachment portions 38 to the papillary muscles 39 (see FIG. 14) in the ventricular cavity 40 when the sewing ring 30 is sutured to the atrio-ventricular junction 41 of the host or patient heart 42, the aggregate area of the cusps 33, 34, 36A and 36B exceeding the area bounded by the sewing ring 30 so that when the valve is caused to open (see FIGS. 3 and 4), by the papillary muscles 39 pulling the chordae 37, the cusps simply deflect away from each other (see particularly FIG. 3), and when the papillary muscles allow the valve to close, the edge portions 33X, 34X and 36X of the cusps meet out of the plane of the sewing ring 30 so as to be capable of meeting in the ventricular cavity 40 of the patient heart.

It should be noted that the chordae 37 from the anterior cusp 33 have been omitted from FIGS. 2 and 4 for the sake of clarity.

The anterior cusp 33 is contiguous with one third of the perimeter of the sewing ring opening 31 and has a generally, semicircular edge portion 33X, to enable it to project deeply into the ventricular cavity 40; and the posterior cusp 34 and lateral cusps 36A and 36B—which are, therefore, together contiguous with two-thirds of the perimeter of the sewing ring opening—also have generally semicircular edge portions 34X and 36X.

The sewing ring 30 is formed by a combination of integral flange portions 43 of the anterior, posterior and lateral cusps stitched to a flat basic ring element 44 cut from bioincorporable material, with a similar flat reinforcing or stiffening ring 45 of bioincorporable material between which and the basic ring element the flange portions of the cusps are interposed (see also FIGS. 7 to 13).

The posterior cusp 34 and the lateral cusps 36A and 36B in the embodiment of FIGS. 1 to 4 are formed from a flat strip of the bioincorporable material, with spacer portions (not shown) between adjacent cusp portions, which spacer portion may be partially cut through and/or pleated and stitched so that the integral flange portion can conform to the arcuate portion 35 of the D-shaped opening, and to bring the adjacent cusp portions into contiguous disposition with each other.

Figure 5:
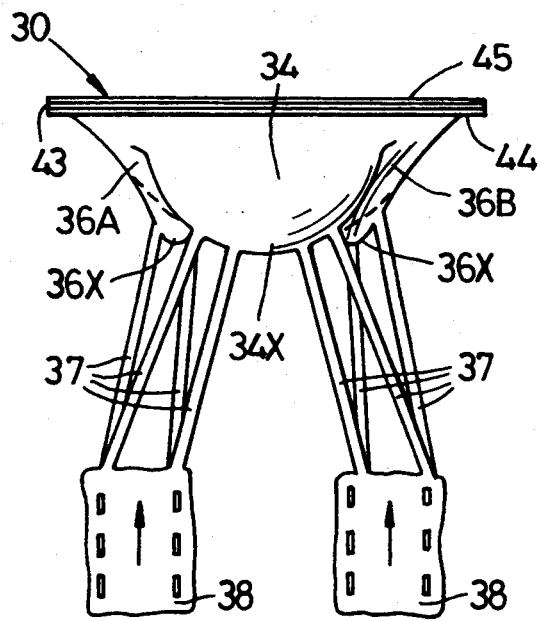
Figure 6:
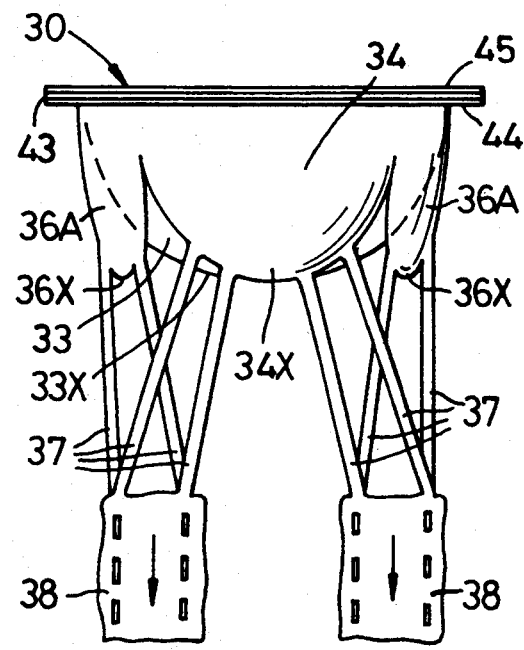
Figure 7:
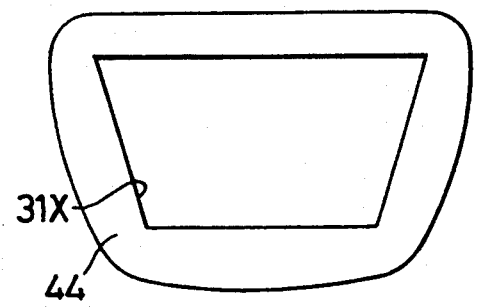
Figure 8:
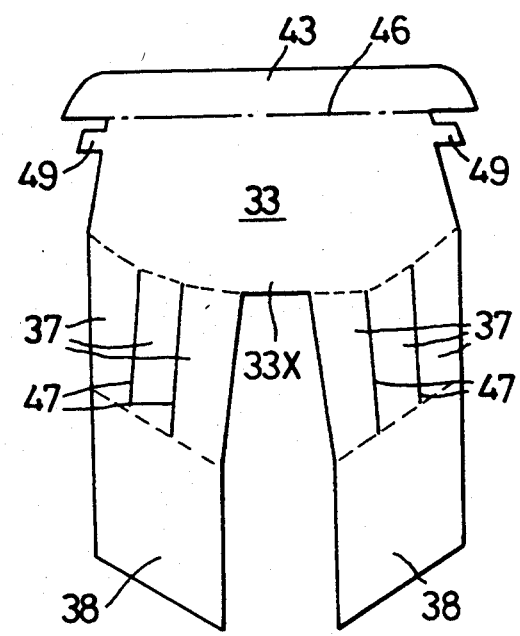

In the embodiment of FIGS. 1 to 4, the chordae 37 are separate chords attached by sewing to the edge portions 33X, 34X and 36X of the cusps and to the attachment portions 38, while in the embodiments of FIGS. 5 and 6 (which otherwise is similar to that of FIGS. 1 to 4) the chordae 37 are formed integral with the cusps and are provided with integral attachment portions 38, those attachment portions integral with the lateral cusps being interposed between attachment portions of the anterior and posterior cusps respectively and stitched together therewith.

In the preferred embodiment of FIGS. 7 to 13, and 19 to 21, the chordae are also formed integral with the cusps and the attachment portions, but all four cusps and their respective chordae 37, attachment portions 38 and flange portions 43 are formed as separate components for fitting to a basic ring element 44 (FIGS. 7 and 13) having a trapezoidal opening 31X, and a reinforcing or stiffening ring element 45 (FIG. 12) is similarly shaped with a trapezoidal opening 31Y. Fold lines between the cusps and their flange portions 43 are indicated by chain dotted lines 46, while ordinary broken or dotted lines distinguish the chordae 37 from the cusps and the attachment portions 38. The chordae of the anterior and posterior cusps 33 and 34 respectively have longitudinal slits 47 which, in use, can open to assist blood flow, while the chordae of the lateral cusps 36A and 36B have slot-like openings 48 for the same purpose, and the slits and slots also facilitate the flexing of the cusps to enable their respective edge portions to meet when the valve closes. Tabs 49 on respective adjacent edges of the cusps adjacent the flange portions 43 are stitched together (FIG. 13) in respective pairs after the flange portions have been stitched on to the basic ring element 44, and the attachment portions 38 of the lateral cusps 36A and 36B are stitched to respective attachment portions of the anterior and posterior cusps 33 and 34 respectively in readiness for suturing to the papillary muscles 39; and, between the tabs 49 and the attachment portions 38 the respective pairs of adjacent edges of the chordae are free to gape (as can be seen in FIG. 13) to assist blood flow.

The surgical procedure involved in inserting the preferred embodiment of the invention will be described with reference to FIGS. 15 to 21, which procedure also involves the use of two other devices in accordance with the invention. The first device is shown in FIGS. 16 to 18 and is a combined sizing and suture placement guiding device 50 comprising an elongate handle 51 carrying an arcuate member 52 having a circumferential shallow groove 53 for fitting within the corresponding part of the remnant 54 (see FIG. 15) of the excised natural valve, with slots 55, one adjacent each end of the arcuate member and one intermediate thereof for indicating the positions of placement sutures 56 (see FIGS. 15 and 20) to be passed also through corresponding positions on the sewing ring 30 of the replacement valve, and with a depth guage 57 consisting of a generally U-shaped bar having a rectilinear base portion 58 to lie across the papillary muscles 39 to indicate the positions (below that base portion 58) for placement sutures 59 in the papillary muscles for securing the attachment portions 38 of the chordae 37.

It will be evident that when the placement sutures 56 and 59 have been inserted the sizing and guiding device 50 is removed to enable the replacement valve to be inserted, which step in the procedure is assisted by a rigid holder 60 which is shown in FIGS. 19 and 20 temporarily secured by tacking stitches 61 to the sewing ring 30. The holder 60 has a generally U-shaped bar 62 extending between the chordae 37 of the anterior and posterior cusps 33 and 34 respectively as far as the attachment portions 38, so as to prevent collapsing of the valve. The holder 60 is also provided with notches 63 for location of the placement sutures 56 previously inserted in the remnant 54 of the excised natural valve. A detachable elongate handle 64 (FIG. 20 only) is attached to the holder 60 to facilitate insertion of the valve as the placement sutures 56 and 59 are drawn through the sewing ring 30 and the attachment portions 38 respectively.

When the placement sutures have been secured, further suturing 65 can be effected all round the sewing ring 30 to complete the procedure.

Figure 16:
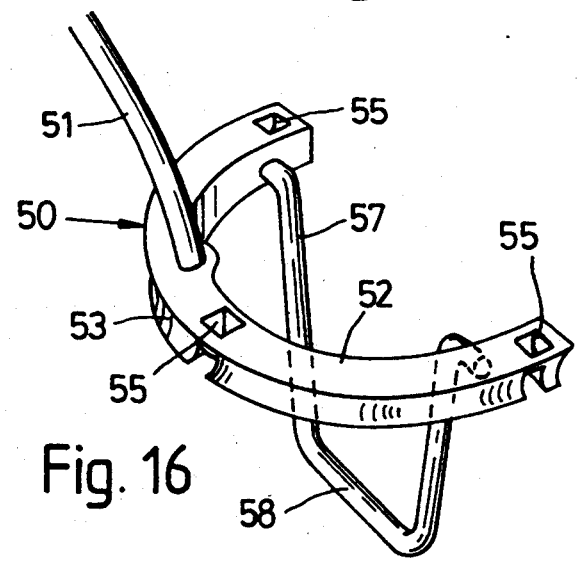
FIG. 16 is a perspective view from above of a combined sizing and suture placement guiding device in accordance with the invention.
Figure 17:
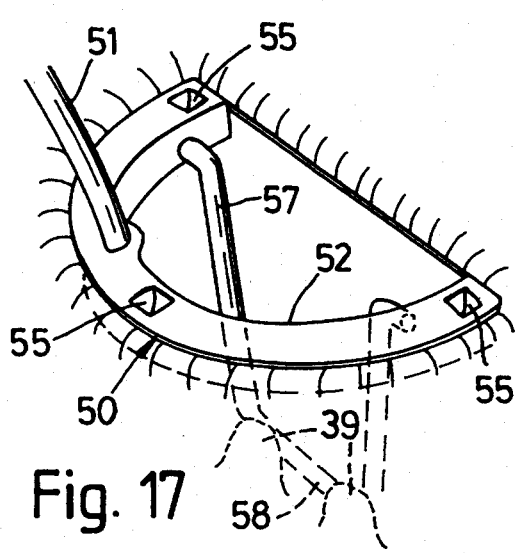
FIG. 17 is a fragmentary perspective view showing the device of FIG. 16 in position.
Figure 18:
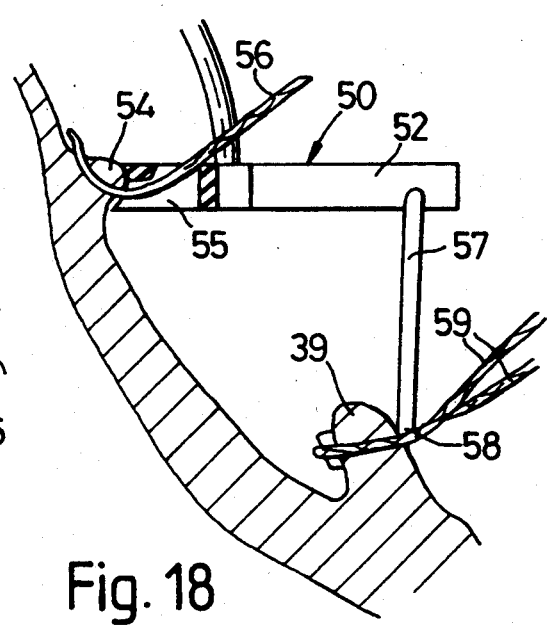
FIG. 18 is a vertical medial section through FIG. 17 showing sutures being positioned.

It will be seen in FIGS. 1 and 3 that the sewing ring 30 has a central broken marker line, which—as shown in FIGS. 19 to 21—can be provided by a suture 66 interwoven into the reinforcing or stiffening ring 45, to indicate inner and outer stitching zones for different ranges of heart sizes, the inner zone being utilized when a smaller sizing device than the device 50 in FIGS. 16 to 18 is found to fit the remnant 54 of the excised natural valve.

I claim:

1. A mitral heart valve replacement of essentially flexible bioincorporable material comprising a generally D-shaped sewing ring having an opening defined by a perimeter including at least one long straight side portion thereof, an anterior cusp hinged contiguously from said straight side portion; a posterior cusp hinged contiguously from a shorter side portion of said opening perimeter opposite said anterior cusp, and two lateral cusps respectively hinged contiguously one from each of two lateral side portions of said opening perimeter extending between adjacent ends of the lateral side portions from which said anterior and posterior cusps are hinged, chordae of bioincorporable material extending from edge portions of said cusps for connection to papillary muscles in a ventricle cavity when the sewing ring is sutured to an atrio-ventricular junction of a host or patient heart, wherein aggregate surface area of said cusps exceeds an area circumscribed by the sewing ring so that when the valve is caused to open, by said papillary muscles pulling the chordae, said cusps simply deflect away from each other, and when said papillary muscles allow the valve to close, the edge portions of the cusps meet within said ventricle cavity of the patient heart.

2. A mitral heart valve replacement as in claim 1, wherein the anterior cusp is contiguous with one-third of said perimeter of the sewing ring opening and has a generally semicircular edge portion to enable it to project deeply into said ventricle cavity, and the posterior and lateral cusps also have generally semicircular edge portions.

3. A mitral heart valve replacement as claimed in claim 1 or claim 2, wherein the sewing ring opening is D-shaped, and is matched by a correspondingly larger D-shaped external profile to suit said atrio-ventricular junction in a patient heart.

4. A mitral heart valve replacement as in claim 1 or claim 2, wherein the sewing ring opening is trapezium-shaped, to provide interrelated longer and shorter parallel straight side portions from which are hinged the anterior and posterior cusps respectively, and two non-parallel side portions from which are hinged the lateral cusps, while the sewing ring has a D-shaped external profile to suit the atrio-ventricular junction in a patient heart.

5. A mitral heart valve replacement as in any one of claims 1 or 2, wherein the sewing ring is formed by a combination of integral flange portions of the anterior, posterior and lateral cusps stitched to a flat basic ring element cut from the bioincorporable material.

6. A mitral heart valve replacement as in claim 5, wherein the flange portions of the cusps are interposed between the basic ring element and a similar flat reinforcing or stiffening element of biocompatible material.

7. A mitral heart valve replacement as in claim 5, wherein the posterior cusp and the lateral cusps and respective integral flange portions thereof are formed from a flat strip of the bioincorporable material, with spacer portions between adjacently located cusp portions, which spacer portions are partially segmented so that said integral flange portion can conform to an arcuate portion of a D-shaped opening, and to bring said adjacently located cusp portions into contiguous disposition with each other.

8. A mitral heart valve replacement as in claim 1 or 2, wherein the chordae are formed integral with the cusps and are provided with integral attachment portions at ends remote from the cusps for suturing to the papillary muscles.

9. A mitral heart valve replacement as in claim 8, wherein the cusps, chordae and attachment portions are provided with non-elastic reinforcing strands running from the cusps to the attachment portions.

10. A mitral heart valve replacement as in claim 9, wherein similar strands also run from side to side of the cusps adjacent their free edges or across the middle.

11. A mitral heart valve replacement as in, claim 1 or 2, wherein the bioincorporable material is biological material, so as to allow the host to cover the valve with living self-repairing fibrous tissue and on this a growth of new endothelium presenting a surface to the blood that does not clot.

12. A mitral heart valve replacement as in claim 1 or 2, wherein the valve is made of a non-biological material that allows the host to provide a cover of fibrous tissue and endothelium leaving the implanted material completely covered by natural host tissue.

13. A mitral heart valve replacement as in, claim 1 or 2, wherein the sewing ring is provided with a central marker line, to indicate inner and outer stitching zones for different ranges of heart size.

14. A mitral heart valve replacement as in claim 13 wherein the marker line is a broken line, formed by an interwoven suture.

15. A mitral heart valve replacement as in, claim 1 or 2, wherein the chordae are separate chords attached by sewing to the edge portions of the cusps and to attachment portions adapted to be eventually sewn to the papillary muscles.

16. A mitral heart valve replacement as in claim 15, wherein said attachment portions of said lateral cusps are secured to adjacently located attachment portions of the anterior and posterior cusps.

17. A mitral heart valve replacement as in claim 16, wherein a rigid holder is temporarily secured to the sewing ring and has a generally U-shaped bar extending between the chordae of the anterior and posterior cusps as far as the attachment portions, so as to prevent collapsing of the valve, particularly during placement in the patient heart.

18. A mitral heart valve replacement as in claim 17, wherein the holder is provided with notches or slots for location of sutures through the sewing ring.

19. A mitral heart valve replacement as in claim 17, wherein the holder has a detachable handle used during placement of the valve in the patient heart.

20. A combined sizing and suture placement guiding device comprising an elongate handle carrying an arcuate sizing member having a circumferential shallow groove for fitting within a corresponding part of a remnant of an excised natural valve of a patient heart at an atrioventricular junction, with notches or slots, one adjacent each end of said sizing member and one intermediate thereof, for indicating positions for placement of sutures to be passed also through corresponding positions on a sewing ring of a replacement valve and with a depth gauge depending from the sizing member for contact with papillary muscles to indicate the positions of placement sutures in papillary muscles for securing attachment portions of connective chordae.

21. A combined sizing and suture placement guiding device as in claim 20 wherein the depth gauge is a generally U-shaped bar having a rectilinear base portion to lie across the papillary muscles.

22. A combined sizing suture and suture placement guiding device as in claim 20 or claim 21 provided with said handle is arranged for assisting placement of the device in the patient heart and removal therefrom.

* * * * *